United States Patent [19]

Loi

[11] Patent Number: 4,787,905

[45] Date of Patent: Nov. 29, 1988

[54] GEL FOR BREAST PROSTHESIS

[75] Inventor: Chay H. Loi, Monterey Park, Calif.

[73] Assignee: Nearly Me, Los Angeles, Calif.

[21] Appl. No.: 77,368

[22] Filed: Jul. 24, 1987

[51] Int. Cl.$^4$ ............................................. A61F 2/52
[52] U.S. Cl. ............................................. 623/7; 623/8; 623/66; 523/113; 524/775
[58] Field of Search ............... 128/DIG. 21; 523/105, 523/113; 524/775; 623/7, 8, 11, 12, 66

[56] References Cited

U.S. PATENT DOCUMENTS

| | | | |
|---|---|---|---|
| 2,345,649 | 4/1944 | Zimmerman et al. | 2/267 |
| 3,020,260 | 2/1962 | Nelson | 260/46.5 |
| 3,067,431 | 12/1962 | Kausch | 3/36 |
| 3,293,663 | 12/1966 | Cronin | 3/36 |
| 3,304,558 | 2/1967 | Mann | 3/36 |
| 3,600,718 | 8/1971 | Boone | 3/36 |
| 3,681,787 | 8/1972 | Perras | 3/36 |
| 3,795,921 | 3/1974 | Zucker | 3/36 |
| 3,807,412 | 4/1974 | Connelly | 128/481 |
| 3,845,507 | 11/1974 | Kirby et al. | 3/36 |
| 3,852,833 | 12/1974 | Koneke et al. | 3/36 |
| 4,125,117 | 11/1978 | Lee | 128/481 |
| 4,168,363 | 9/1979 | Boettcher | 528/75 |
| 4,172,298 | 10/1979 | Rechenberg | 3/36 |
| 4,199,825 | 4/1980 | Knoche | 3/36 |
| 4,247,351 | 1/1981 | Rechenberg | 156/221 |
| 4,249,975 | 2/1981 | Rechenberg | 156/245 |
| 4,316,832 | 2/1982 | Walkden | 524/775 |
| 4,375,521 | 3/1983 | Arnold | 524/297 |
| 4,401,492 | 8/1983 | Pfrommer | 156/61 |
| 4,404,296 | 9/1983 | Schapel | 523/105 |
| 4,517,326 | 5/1985 | Cordts et al. | 524/310 |
| 4,666,968 | 5/1987 | Downey et al. | 524/775 |

Primary Examiner—Richard J. Apley
Assistant Examiner—Paul Prebilic
Attorney, Agent, or Firm—Herzig & Yanny

[57] ABSTRACT

The invention relates to a method of producing a new and novel gel composition suitable for use in breast prostheses, including a mixture of hydroxyl terminated polybutadiene resin, diundecyl phthalate, polymethylene polyphenyl isocyanate, and dibutyltin dilaurate catalyst, allowing the mixture to stand, and curing the mixture.

2 Claims, No Drawings

GEL FOR BREAST PROSTHESIS

BACKGROUND OF THE INVENTION

1. Field of the Invention

The invention herein embodies prosthetics and, more particularly, a method for manufacturing a gel for use in breast prostheses.

2. Brief Description of Prior Art

It is conventional practice following post-mastectomy surgery to have the patient fitted with a breast prosthesis to augment that portion of the pectoral area which has been removed. The selection and purchase of such a prosthesis is much more complicated than that of almost any other prosthetic body part. Present breast prostheses are composed of cells in which a substance which is supposed to duplicate characteristics of the human breast material is contained. However, materials chosen often have characteristics different from the human breast material. Therefore, the prosthesis does not have the desireddegree of flexibility and texture, and does not have the capability of moving with the body during physical activities in such a way as to simulate or duplicate the characteristics of a natural breast. Many of these materials harden after washing, are irritating to the skin, or feel unnatural or uncomfortable.

The use of air filling has been taught in U.S. Pat. No. 3,852,833 in an attempt to effect the natural contouring of the breast. The use of an air filling can lead to an unavoidable "bowing" effect which entails a formation of a spherical shape, as opposed to the natural contours of the body of the wearer. Material suggested for use as the filler for breast prostheses also include bags of silicone and glycerin, silicone foam or gel pads, or silicone pads filled with air.

Additionally, U.S. Pat. No. 3,795,921 suggests chips of a foam rubber substance to approximate the size and elasticity of a natural breast.

SUMMARY OF THE INVENTION

The invention provides a method for producing a gel suitable for use in breast prostheses comprising: Forming a mixture of (by weight percent) 9.9% hydroxyl terminated polybutadiene resin, 89.1% diundecyl phthalate, 0.9% polymethylene polyphenyl isocyanate, and 0.1% dibutyltin dilaurate catalyst; allowing the mixture to stand for about 16 hours; and curing the mixture for at least two hours at a temperature of 93° C. (200° F.).

DETAILED DESCRIPTION OF A PREFERRED EMBODIMENT

To test the characteristics of any gel form, an instrument named the "Precision Penetrometer" (manufactured by Precision Scientific Co.) is used. The instrument can be described briefly as containng a weighted probe that is allowed to drop from a standard position into cup of test material. The weighted probe deforms the test material a certain distance, which is reflected on a readout dial. Scores of around 180 are regarded as showing desirable characteristics for the test material use in filling a breast prosthesis cell.

To prepare a mixture for forming the gel used in breast prostheses cells, a first mixture is prepared consisting of around 10% hydroxyl terminated polybutadiene resin and 90% diundecyl phthalate. The polybutadiene resin can be the product POLY BD®2800 Resin provided by Arco Chemical Company. The Diundecyl Phthalate is a product name of Monsanto Chemical Company for their 1,2-benzenedicarboxylic acid, diundecyl ester. To this first mixture is added 0.9% polymethylene polyphenyl isocyanate and 0.1% dibutyltin dilaurate catalyst. One specific methane diisocyanate that can be used is PAPI®901 Polymeric methane diisocyanate produced by Dow Chemical. One type of dibutyltin dilaurate catalyst can be DABCO®T-12 Catalyst produced by Air Products and Chemicals, Inc.

After thorough mixing, these components are allowed to stand for about 16 hours. After standing, the mixture is cured in an oven at a temperature of at least 93° C. (200° F.).

Testing these mixtures as produced above, gave the following results on the Precision Penetrometer:

| Ratio | 24 Hours | 48 Hours |
| --- | --- | --- |
| [43.42 gr (PAPI 901) [4.58 gr (T12) [5000 gr (D.U.P. mixture - 4,500 gr D.U.P. plus 500 gr POLY BD ® ) | P = 210 | P = 120 |
| [45.20 gr (PAPI 901) [4.58 gr (T12) [5000 gr (D.U.P. mixture - 4,500 gr D.U.P. plus 500 gr POLY BD ® ) | P = 170 | P = 75 |
| [47.02 gr (PAPI 901) [4.58 gr (T12) [5000 gr (D.U.P. mixture - 4,500 gr D.U.P. plus 500 gr POLY BD ® ) | P = 110 | P = 40 |
| [48.80 GR (PAPI 901) [4.58 gr (T12) [5000 gr (D.U.P. mixture - 4,500 gr D.U.P. plus 500 gr POLY BD ® ) | P = 80 | P = 10 |

Those skilled in the art will quickly realize that a gel prosthesis formed in accordance with the method of the present invention may utilize a variety of mixture proportions. In any event, the other mixtures will nevertheless employ the present invention as defined in the following claim.

I claim:

1. A method of producing a gel suitable for use in breast prostheses, comprising:
   forming a mixture of, by weight percent, 9.9% hydroxyl terminated polybutadiene resin and 89.1% 1,2-benzenedicarboxylic acid, diundecyl ester, 0.9% polymethylene polyphenyl isocyanate and 0.1% dibutyltin dilaurate catalyst;
   allowing the mixture to stand for about 16 hours; and
   curing the mixture at least two hours at a temperature of 93° C. (200° F.).

2. A gel suitable for use in breast prostheses consisting essentially of, by weight percent, 9.9% hydroxyl terminated polybutadiene resin, 89.1% 1,2-benzenedicarboxylic acid diundecyl ester, 0.9% polymethylene polyphenyl isocyanate, and 0.1% dibutyltin dilaurate catalyst wherein the components are thoroughly mixed, allowed to stand for about 16 hours and cured for at least two hours at a temperature of 93° C. (200° F.) thereby resulting in a gel having, after 24 hours, a recording of about 180 on the precision penetrometer.